United States Patent
Gilboa-Solomon et al.

(10) Patent No.: US 11,636,638 B2
(45) Date of Patent: Apr. 25, 2023

(54) SYSTEMS AND METHODS FOR GENERATING SUMMARY MEDICAL IMAGES

(71) Applicant: International Business Machines Corporation, Armonk, NY (US)

(72) Inventors: Flora Gilboa-Solomon, Haifa (IL); Aviad Zlotnick, Netofah (IL)

(73) Assignee: International Business Machines Corporation, Armonk, NY (US)

(*) Notice: Subject to any disclaimer, the term of this patent is extended or adjusted under 35 U.S.C. 154(b) by 321 days.

(21) Appl. No.: 16/942,805

(22) Filed: Jul. 30, 2020

(65) Prior Publication Data
US 2022/0036612 A1  Feb. 3, 2022

(51) Int. Cl.
| | | |
|---|---|---|
| G06T 11/60 | (2006.01) | |
| G16H 30/40 | (2018.01) | |
| G16H 50/20 | (2018.01) | |
| G06K 9/62 | (2022.01) | |
| G06N 20/00 | (2019.01) | |
| G06V 10/40 | (2022.01) | |

(52) U.S. Cl.
CPC ........... G06T 11/60 (2013.01); G06K 9/6215 (2013.01); G06N 20/00 (2019.01); G06V 10/40 (2022.01); G16H 30/40 (2018.01); G16H 50/20 (2018.01); *G06T 2210/41* (2013.01)

(58) Field of Classification Search
CPC ........ G06T 11/60; G16H 50/20; G16H 30/40; G06N 20/00; G06V 10/40; G06K 9/6215
See application file for complete search history.

(56) References Cited

U.S. PATENT DOCUMENTS 8,472,691 B2 * 6/2013 Furst .................... G06V 20/647
705/2
2008/0130833 A1  6/2008 Wang

FOREIGN PATENT DOCUMENTS

WO  2018026431 A1  2/2018

* cited by examiner

*Primary Examiner* — Edward Park
(74) *Attorney, Agent, or Firm* — Roy S. Melzer

(57) ABSTRACT

There is provided a computer implemented method for generating summary images from 3D medical images, comprising: receiving a 3D medical image, dividing the 3D medical images into a sequence of a plurality 2D images, computing a similarity dataset indicative of an amount of similarity between each pair of the plurality of 2D images, segmenting the similarity dataset into a plurality of slabs by minimizing the amount of similarity between consecutive slabs and maximizing the amount of similarity within each slab, aggregating, for each respective slab, the plurality of 2D images into a respective summary image, and presenting on a display, the respective summary image.

13 Claims, 3 Drawing Sheets

SYSTEMS AND METHODS FOR GENERATING SUMMARY MEDICAL IMAGES

BACKGROUND

The present invention, in some embodiments thereof, relates to medical image processing and, more specifically, but not exclusively, to a systems and methods for generating summary medical images from 2D and/or 3D medical images.

Two-and-a-half dimensional (2.5D) images are two dimensional (2D) images that simulate the appearance of being three dimensional (3D) images. A single 2.5 medical image may be created from a 3D dataset of a 3D image, for example, a CT scan, to help the radiologist gain a view of the 3D image dataset as a whole, in addition or as an alternative to, scrolling through 2D slices of the 3D medical image.

SUMMARY

According to a first aspect, a computer implemented method for generating summary images from 3D medical images, comprises: receiving a 3D medical image, dividing the 3D medical images into a sequence of a plurality 2D images, computing a similarity dataset indicative of an amount of similarity between each pair of the plurality of 2D images, segmenting the similarity dataset into a plurality of slabs by minimizing the amount of similarity between consecutive slabs and maximizing the amount of similarity within each slab, aggregating, for each respective slab, the plurality of 2D images into a respective summary image, and presenting on a display, the respective summary image.

According to a second aspect, a computer implemented method for generating summary images from sequentially acquired real time 2D medical images, comprises: in a plurality of iterations: receiving a 2D medical image captured in real time, computing an amount of similarity between the 2D medical image and at least one previously obtained sequence of 2D medical images, in response to the amount of similarity being below a threshold, determining that the 2D medical image represents an end of a slab of a plurality of sequentially obtained 2D medical images, aggregating the plurality of sequentially obtained 2D images of the slab into a summary image, and presenting the summary image on a display.

According to a third aspect, a computer implemented method for generating summary images from 3D medical images, comprises: receiving a 3D medical image, dividing the 3D medical images into a sequence of a plurality 2D images, computing a similarity dataset indicative of an amount of similarity between each pair of the plurality of 2D images, segmenting the similarity dataset into a plurality of slabs by minimizing the amount of similarity between consecutive slabs and maximizing the amount of similarity within each slab, aggregating, for each respective slab, the plurality of 2D images into a respective summary image, inputting each respective summary image into a summary machine learning model trained on a training dataset of a plurality of sample summary images and corresponding at least one finding depicted therein indicative of ground truth, and obtaining a score indicative of at least one finding depicted in the summary image as an outcome of the summary machine learning model.

In a further implementation form of the first aspect, aggregating comprises computing, for each respective slab, a maximum intensity projection (MIP) from the plurality of 2D images, wherein the summary image comprises the MIP.

In a further implementation form of the first aspect, further comprising: selecting a sub-sample set of at least one 2D image from each respective slab, wherein the sub-sample includes fewer 2D images than the respective slab, inputting each 2D image of each respective sub-sample set of each respective slab into a 2D machine learning model trained on a training dataset of a plurality of sample 2D images and corresponding at least one visual feature depicted therein indicative of ground truth, and obtaining a score indicative of the presence of at least one finding depicted in each 2D image as an outcome of the 2D machine learning model.

In a further implementation form of the first aspect, the sub-sample set includes at least one boundary 2D image that is sequentially adjacent to another slab.

In a further implementation form of the first aspect, the 2D machine learning model includes a simple deep neural network (DNN) and excludes a feature pyramid that processes inputted 3D images in a plurality of resolutions and with a plurality of box shapes.

In a further implementation form of the first aspect, the similarity dataset is a matrix of size N×N wherein N denotes a number of the plurality of 2D images.

In a further implementation form of the first aspect, further comprising: inputting each 2D image into a neural network trained to analyze a target 2D image and output an indication of a target visual feature being depicted within the target 2D image, extracting, for each 2D image, a feature vector from the neural network, wherein the amount of similarity is computed for the feature vectors of each pair.

In a further implementation form of the first aspect, the amount of similarity is computed for the feature vectors of each pair using a cosine similarity.

In a further implementation form of the first aspect, the feature vector is selected from the group consisting of: embeddings obtained from hidden layers of the neural network, an output of an autoencoder implementation of the neural network, and the feature vector is an output of the neural network.

In a further implementation form of the first aspect, further comprising selecting the neural network from a plurality of neural networks each trained to output an indication of a different visual feature, according to the visual feature, wherein the user is viewing the 3D medical image to search for the visual feature.

In a further implementation form of the first aspect, the plurality of slabs are computed by inputting the sequential 2D images into a video scene analysis process that divides a video into scenes of frames, the 2D images corresponding to frames of the video and the scenes corresponding to slabs.

In a further implementation form of the first aspect, the 3D medical image is selected from the group consisting of: CT, MRI, breast tomography, 3D ultrasound, 3D nuclear imaging, and PET.

In a further implementation form of the first aspect, the 3D medical images are divided into a sequence of a plurality 2D images according to a slice orientation and/or a slice thickness defined by the user viewing the plurality of 2D images and corresponds to the slice orientation and/or slice thickness when the user views the plurality of 2D images.

In a further implementation form of the second aspect, aggregating comprises computing, for each respective slab, a maximum intensity projection (MIP) from the plurality of 2D images, wherein the summary image comprises the MIP.

In a further implementation form of the second aspect, further comprising: inputting at least one respective summary image into a summary machine learning model trained on a training dataset of a plurality of sample summary images and corresponding at least one visual feature depicted therein indicative of ground truth, and obtaining at least one visual finding depicted in the summary image as an outcome of the summary machine learning model.

In a further implementation form of the second aspect, further comprising: in response to the amount of similarity being above a threshold indicating that the 2D medical image does not represent the end of the slab, including the 2D medical image as part of the slab, and performing another iteration by receiving another 2D medical image.

In a further implementation form of the second aspect, the 2D medical image and the sequence of 2D images are captured by an imaging device selected from the group consisting of: colonoscope, endoscope, bronchoscope, and 2D ultrasound.

In a further implementation form of the second aspect, further comprising: inputting the 2D medical image into a neural network trained to analyze a target 2D medical image and output an indication of a target visual feature being depicted within the target 2D medical image, and extracting, for the 2D medical image, a feature vector from the neural network, wherein computing the amount of similarity comprises computing the amount of similarity between the feature vector of the 2D medical image and feature vectors of the plurality of sequentially obtained 2D medical images.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1A:
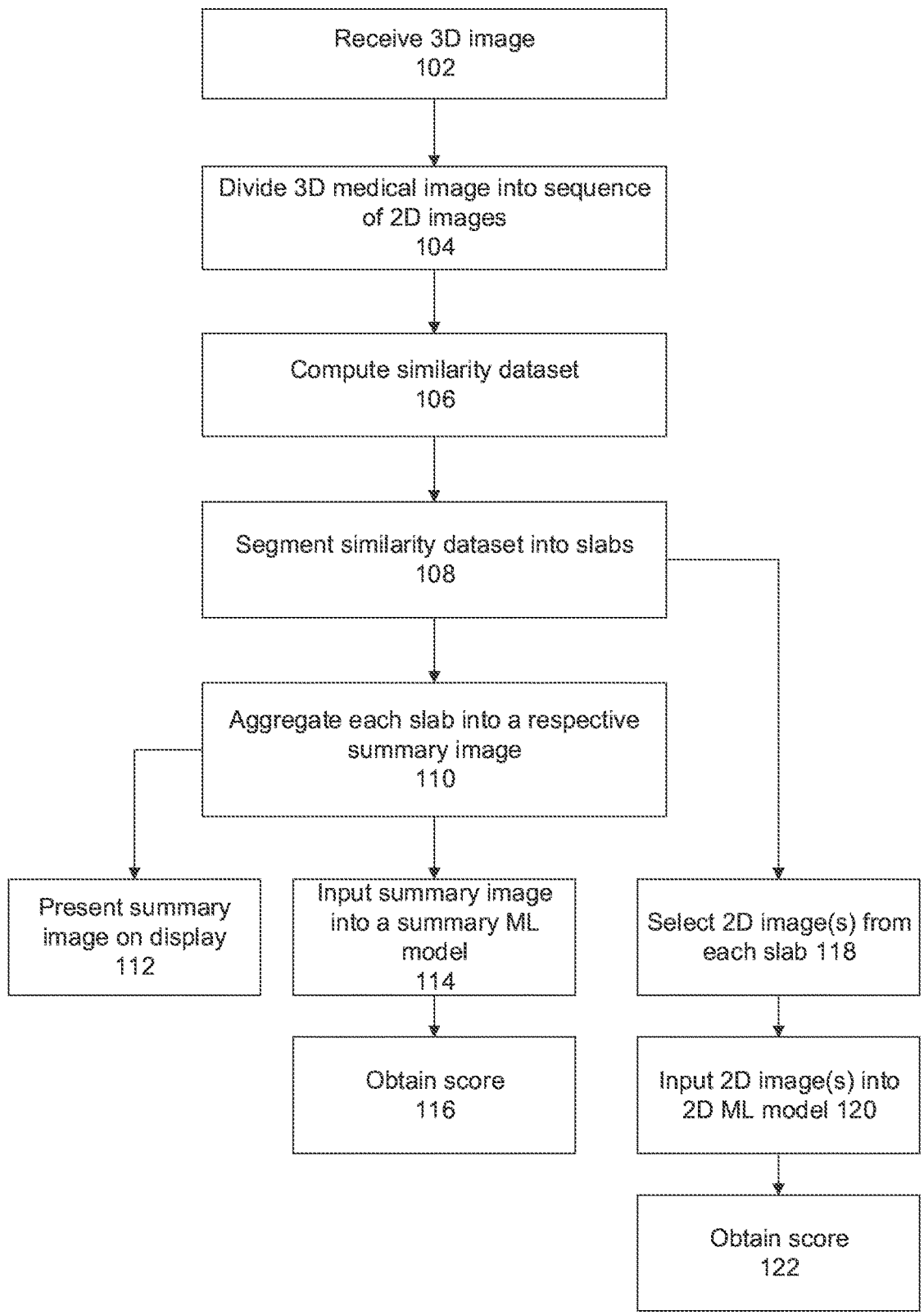
FIG. 1A is a flowchart of a method for computing a summary image from slabs of 2D images of a 3D image, in accordance with some embodiments of the present invention.

The present invention, in some embodiments thereof, relates to medical image processing and, more specifically, but not exclusively, to a systems and methods for generating summary medical images from 2D and/or 3D medical images.

An aspect of some embodiments of the present invention relates to systems, methods, an apparatus, and/or code instructions (i.e., stored on a memory and executable by at least one hardware processor) for generating one or more summary images from 3D medical images, and/or from sequential 2D medical images which may be real time images and/or viewed off line, sometimes referred to herein as frames (e.g., obtained during a colonoscopy, bronchoscopy, 2D ultrasound). Each summary image summarizes a portion of the 3D image. Each summary includes and/or is computed from a subset of 2D images of the 3D medical image, and/or a subset of the real time 2D frames. The summary images may be presented on a display for viewing by a user, and/or inputted into a trained summary machine learning (ML) model that generates an outcome of a score indicative of one or more findings found in the summary image. Clinically significant findings may be expected to be found in a small number of summary images, or in a single summary image. For example, a single summary image of a CT scan (which may correspond to 3-5 2D slices of the CT scan) may depict a lung nodule being evaluated for lung cancer, and/or a single summary image (e.g., including 20-100 video frames of a colonoscopy video) may depict a small colon polyp.

Alternatively or additionally, a subsample of 2D images of a slab of 2D images that may be used to compute the summary image is selected. The subsample of 2D images may be inputted into a trained 2D ML that generates an outcome of a score indicative of one or more findings found in the respective 2D image. Analyzing the subsample of 2D images for the presence of findings may be significantly more computationally efficient (e.g., using fewer processing resources, less memory, and/or takes less processing time) than analyzing the whole 3D image, the portion of the 3D image, and/or analyzing or all of the 2D slices, using respective ML models, for example, using an ML model designed to process 3D volumetric image data.

For the case of 3D images, the 3D medical image is divided into a sequence of 2D images (sometimes referred to herein as slices). A similarity dataset indicative of an amount of similarity between each pair of sequential 2D images is computed. The similarity dataset and/or the sequence of 2D images corresponding to the similarity dataset are segmented into slabs by minimizing the amount of similarity between consecutive slabs and maximizing the amount of similarity within each slab. Each slab includes one or more 2D images. The 2D images of each respective slab are aggregated into a respective summary image. Each respective summary image may include and/or be computed from a sequence of 2D images that summarize a portion of the 3D image. In some embodiments, each respective summary image may be a 2D image that simulates an appearance of being a 3D image. In an exemplary implementation, the summary image is computed from the 2D images of the respective slab by computing a maximum intensity projection (MIP) from the 2D images. The summary image is defined by the MIP. Each summary may be presented on a display, and/or inputted into a machine learning model trained on a training dataset of sample summary images and corresponding findings depicted in the corresponding summary image indicative of ground truth. A score indicative of the presence of at least one finding depicted in the summary image is obtained as an outcome of the machine learning model. For example, likelihood of a pulmonary nodule being present in the respective summary image.

The amount of similarity of the similarity dataset may be computed by inputting each 2D image (obtained by dividing the 3D image) into a neural network trained to analyze a target 2D image and output an indication of a target visual feature being depicted within the target 2D image. For each 2D image, a feature vector is extracted from the neural network, for example, embeddings (e.g., weights of the neurons) of one or more hidden layers of the neural network and/or output of an encoder implementation of the neural network. The amount of similarity is computed for the feature vectors of each pair, for example, using a cosine similarity computed for each pair. The similarity dataset is segmented into multiple groups by minimizing the amount of similarity between consecutive groups and maximizing the amount of similarity within each group. 2D images included within each group are more similar to each other than to other 2D images of other groups. Each group corresponds to one slab.

For the case of real time sequential 2D images, each newly currently captured frame (i.e., 2D image) is analyzed to determine whether the current frame is part of the current slab, or whether the current frame forms a new slab. Once the complete slab has been identified, the summary image is computed by aggregating the 2D image of the complete slab. It is noted that in the case of streaming videos, each slab may correspond to a certain anatomical region. For example, after the colonoscope has been moved to another region in the colon, a new slab is identified. Each summary image may depict a different anatomical region.

At least some implementations of the systems, methods, apparatus, and/or code instructions described herein relate to the technical problem of improving visibility of visual features captured in 3D imaging data, for example, captured by CT, MRI, PET, and a 3D mammogram. At least some implementations of the systems, methods, apparatus, and/or code instructions described herein relate to the technical problem of improving visibility of visual features captured in real time 2D imaging data, for example, captured by a colonoscope, endoscope, bronchoscope, and/or 2D ultrasound.

At least some implementations of the methods, systems, apparatus, and/or code instructions described herein address the technical problem, which may be a medical problem, of missing important visual findings during reading of 3D medical images. For example, a radiologist scanning an abdominal CT scan may miss a small tumor located in the liver. Radiologists manually scan 3D medical images one 2D slice at a time, until the entire 3D medical image is covered. Manual analysis of 3D medical images, such as Digital Breast Tomosynthesis (DBT), CT, and MRI, requires much more time than analyzing 2D images, since there is much data to process. For example, a chest and abdomen CT scan may include hundreds of 2D slices, each of which require manual reading by the radiologist. However, using 3D data has advantages over 2D data, so using only 2D data is not relevant. For example, the 3D data improves the diagnostic abilities, since visual findings may be traced along multiple sequential 2D slices, for example, aortic aneurysms appear on multiple sequential slices. Since time is limited, and the radiologist is required to browse though many 2D slices during the limited available time, the radiologist may miss some 2D slices, or not spend sufficient time on some 2D slices, potentially missing clinically significant visual findings.

At least some implementations of the methods, systems, apparatus, and/or code instructions described herein address the technical problem, which may be a medical problem, of missing important visual findings during reading of sequential 2D images, which may be real time images (and/or images viewed offline), obtained during an imaging procedure session, for example, colonoscopy, bronchoscopy, endoscopy, and 2D ultrasound imaging. For example, a gastroenterologist scanning real time 2D images of the colon during a colonoscopy may miss a small polyp located in the colon. Gastroenterologists manually scan 2D medical images one 2D image at a time, until the entire anatomical region, for example, the colon, has been visually inspected. Since small visual features such as small polyps appear in a small number of the 2D images, such visual features may be missed.

At least some implementations of the systems, methods, apparatus, and/or code instructions described herein improve the technology of medical image processing, by dividing a 3D medical image into slabs of 2D images. At least some implementations of the systems, methods, apparatus, and/or code instructions described herein improve the technology of medical image processing, by arranging sequentially acquired real time 2D images into slabs of 2D images. 2D images in each slab are similar (or more similar) to each other, and 2D images of different slabs are non-similar (or less similar) to each other. The similarity may be computed for encodings extracted from a neural network (or other machine learning process) trained to identify target visual findings in each 2D image. In some embodiments, the encodings of the 2D images of each slab are similar in terms of similar target visual findings (i.e., content). In some embodiments, encodings of 2D images of different slabs are different in terms of different target visual findings. 2D images of each slab may be aggregated into a summary image, which improves the visibility of the target visual findings that are depicted within the respective slab. None relevant and/or less similar 2D images (i.e., of other slabs) are excluded from the created summary image, and may be included in another summary image created from another slab.

Traditional approaches to viewing 3D imaging data are by examining 2D slices of the 3D image. For example, the radiologist scrolls through sequential 2D slices of the 3D scan, examining one 2D slice at a time. Some features, such as calcification clusters are difficult to spot in single 2D slices, for example, calcification buildup on walls of an artery may be thin and difficult to see in a single 2D slice. Radiologists, when they spot such finding, may scroll forward and backward along the sequential 2D slices in order to try and get a better idea of what the visual finding looks like. Other approaches create a single 2D image from the whole set of 3D image data, for example, by performing construction based on alignment of the slices. The single 2D image created from the set of 3D image data loses too much information along the way, increasing the risk that important visual findings in a small part of the 3D image (e.g., appearing in one or a small number of 2D slices) are lost, and/or increasing the risk that the clinically important visual findings are drowned by other more prominent non-clinically significant visual findings. The 2D image is created from the 3D image without any reference to the content of the image data. In contrast, at least some implementations of the systems, methods, apparatus, and/or code instructions described herein, created summary images from 2D images which have similar content depicted therein.

At least some implementations of the systems, methods, apparatus, and/or code instructions described herein relate to the technical problem of reducing computational resources of processing 3D medical images, for example, captured by CT, MRI, PET, and a 3D mammogram. At least some implementations of the systems, methods, apparatus, and/or code instructions described herein relate to the technical problem of reducing computational resources of processing a large number of real time sequential 2D images, for example, a video, for example, captured by a colonoscope, bronchoscope, endoscope, and/or 2D ultrasound. At least some implementations of the systems, methods, apparatus, and/or code instructions described herein improve a computer processing 3D medical images and/or large number of 2D real time images, by reducing the computations resources required to process the 3D medical images and/or large number of 2D real time images in a reasonable time, and/or by reducing the time to process the 3D medical images and/or large number of 2D real time images using existing resources. Processing 3D medical images and/or large number of 2D real time images requires a significant amount of processing resources and/or memory resources, due to the large amount of data stored in 3D medical images and/or the large number of real time 2D images. Processing such 3D medical images and/or large number of 2D real time images requires a significant amount of time, making processing of a large number of 3D images and/or large number of 2D real time images, impractical. For example, neural networks that apply 3D convolutions take a significant amount of time and/or uses a significant amount of computational resources to process 3D images. In another example, inputting each frame of a video into a neural network takes a significant amount of time and/or uses a significant amount of computational resources to process all of the frames of the video. Some approaches process 2D data extracted from the 3D medical images, and/or a subset of 2D images of each slab, since neural networks that process 2D images take less time and/or use fewer computational resources and/or processing a sample of 2D images takes less time and/or use fewer computational resources that processing all of the 2D images of the slab.

At least some implementations of the systems, methods, apparatus, and/or code instructions described herein provide a solution to the above mentioned technical problem and/or improve the computer processing 3D images, by dividing the 3D medical image into slabs of 2D images. 2D images in each slab are similar (or more similar) to each other, and 2D images of different slabs are non-similar (or less similar) to each other. The similarity may be computed for encodings extracted from a neural network (or other machine learning process) trained to identify target visual findings in each 2D image. The neural network from which encodings are extracted may be executed using few computational resources and/or in limited time, enabling efficient processing of all 2D slices. In some embodiments, the encodings of the 2D images of each slab are similar in terms of similar target visual findings (i.e., content). In some embodiments, encodings of 2D images of different slabs are different in terms of different target visual findings. One or more 2D images (optionally a single 2D image) are sampled from each slab, and fed into a machine learning model for processing thereof. Processing the sampled 2D images using the machine learning model uses fewer computational resources and/or is performed in less time than using the machine learning model to process the 3D image. Rather than analyzing each one of the 2D images of the slab by inputting each 2D imaging into the 2D ML model, the sub-sample images are analyzed by being inputted into the 2D ML model, which provides an overall state of the slab while significantly reducing the amount of computational resources used to analyze the model. Alternatively or additionally, the summary image, which is created by aggregating the 2D images of each respective slab, is fed into the machine learning model.

However, processing such 2D data incurs the risk that clinically important information that is captured in the 3D image is not present or not significantly present in the 2D data, increasing likelihood of missing such clinically significant findings. The technical problem is addressed by at least some implementations of the systems, methods, apparatus, and/or code instructions described herein, by arranging the 2D slices into slabs, and optionally selecting 2D images from each slab. The slabs, which are computed as described herein, are more likely to depict the clinically important information therein. Therefore, analyzing the slab or selected 2D images of the slab is likely to avoid or reduce missing the clinically important information.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 1B:
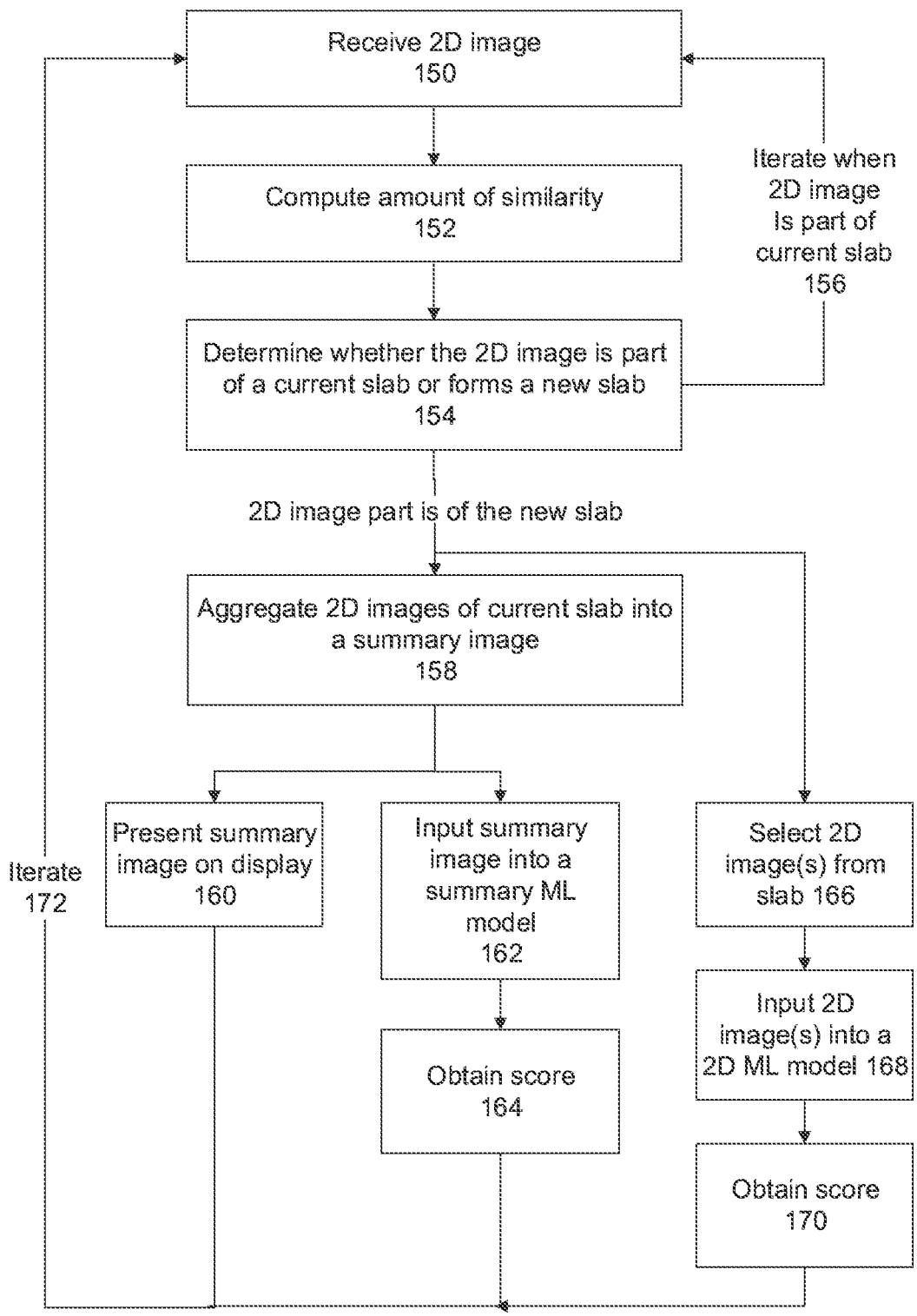
FIG. 1B is a flowchart of a method for computing a summary image from slabs of a sequence of 2D images acquired in real time, in accordance with some embodiments of the present invention.
Figure 2:
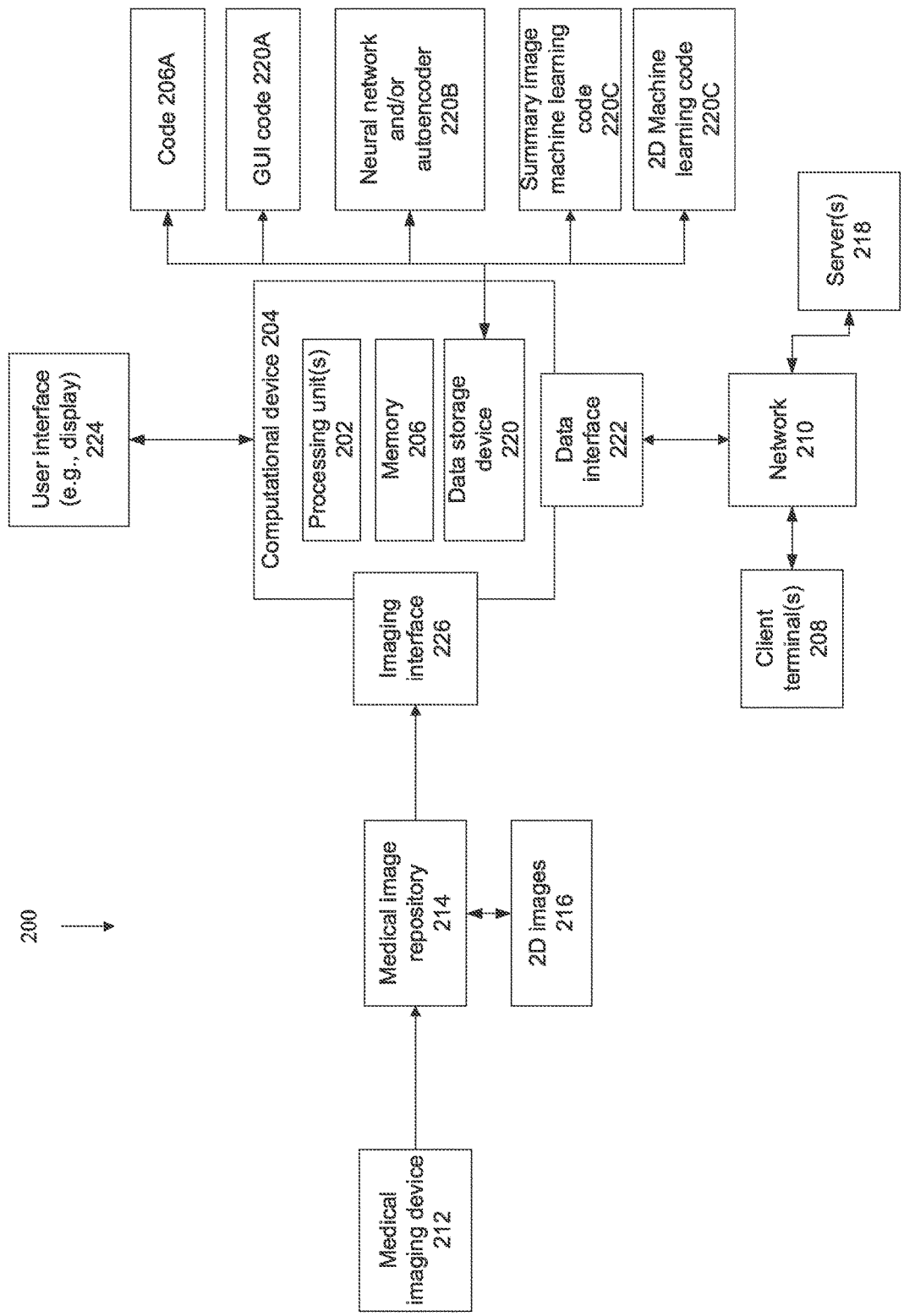
FIG. 2, which is a block diagram of components of a system 200 for computing a summary image from slabs of 2D images of a 3D images and/or slabs of a sequence of 2D images acquired in real time, in accordance with some embodiments of the present invention.

Reference is now made to FIG. 1A, which is a flowchart of a method for computing a summary image from slabs of 2D images of a 3D image, in accordance with some embodiments of the present invention. Reference is also made to FIG. 1B, which is a flowchart of a method for computing a summary image from slabs of a sequence of 2D images acquired in real time, in accordance with some embodiments of the present invention. Reference is also made to FIG. 2, which is a block diagram of components of a system 200 for computing a summary image from slabs of 2D images of a 3D images and/or slabs of a sequence of 2D images acquired in real time, in accordance with some embodiments of the present invention. System 200 may implement the features of the method described with reference to FIG. 1A-1B, by one or more hardware processors 202 of a computing device 204 executing code instructions stored in a memory (also referred to as a program store) 206.

Computing device 204 may be implemented as, for example, a client terminal, a server, a radiology workstation, a virtual machine, a virtual server, a computing cloud, a mobile device, a desktop computer, a thin client, a Smartphone, a Tablet computer, a laptop computer, a wearable computer, glasses computer, and a watch computer.

Computing device 204 may include an advanced visualization workstation that sometimes is add-on to a radiology workstation and/or other devices.

Computing device 204 and/or client terminals 208 and/or servers 218 may be implemented as, for example, radiology workstations, image viewing stations, picture archiving and communication system (PACS) server, and electronic medical record (EMR) server.

Multiple architectures of system 200 based on computing device 204 may be implemented. In an exemplary implementation, computing device 204 storing code 206A may be implemented as one or more servers (e.g., network server, web server, a computing cloud, a virtual server) that provides services (e.g., one or more of the acts described with reference to FIG. 1) to one or more servers 218 and/or client terminals 208 over a network 210, for example, providing software as a service (SaaS) to the servers 218 and/or client terminal(s) 208, providing software services accessible using a software interface (e.g., application programming interface (API), software development king (SDK)), providing an application for local download to the servers 218 and/or client terminal(s) 208, and/or providing functions using a remote access session to the servers 218 and/or client terminal(s) 208, such as through a web browser and/or viewing application. For example, users use client terminals 208 to access computing device 204 acting as a PACS server or other medical image storage server. Computing device 204 computes the summary image(s) from a 3D medical image provided by the client terminal 208 and/or obtained from another data source (e.g., PACS server). The summary image(s) may be provided to the client terminal 208 for presentation on a display of client terminal 208 and/or provided for further processing and/or stored. Alternatively or additionally, the summary image(s) is inputted into one or more trained machine learning models 220B to obtain a score as an outcome. The score may be provided to the client terminal 208 and/or provided for further processing and/or stored. Other features may be performed centrally by computing device 204 and/or locally at client terminal 208. In another implementation, computing device 204 may include locally stored software (e.g., code 206A) that performs one or more of the acts described with reference to FIG. 1A-1B, for example, as a self-contained client terminal and/or server. The summary image may be locally computed from 3D image and/or 2D frames, and the summary image may be presented on a display of computing device 204. In yet another implementation, server 218 is implemented as the medical image storage server. Users use client terminals 208 to access the summary image(s) from server 218. The summary image(s) may be local computed by server 218 and/or by computing device 204, using the 3D image and/or 2D frames which may be stored on server 218 and/or at another location. The summary image is presented on the display of client terminals 208. Computing device 204 may provide enhanced features to the image server 218, by computing summary images from 3D images and/or real time frames stored by the image server 218. For example, PACS server 218 communicates with computing device 204 using an API, to transfer the 3D image and/or summary image to computing device 204 and receive the computed summary image(s).

Computing device 204 receives 3D medical images and/or 2D images (e.g., obtained in real time) captured by a medical imaging device(s) 212. The medical imaging device 212 may capture 3D images, for example, CT, MRI, breast tomography, 3D ultrasound, and/or nuclear images such as PET. Alternatively or additionally, the medical imaging device 212 may capture 2D images, optionally in real time, for example, colonoscope, bronchoscope, endoscope, and 2D ultrasound.

Medical images captured by anatomical imaging device 212 may be stored in an anatomical image repository 214, for example, a storage server, a computing cloud, a virtual memory, and a hard disk. The 2D slices 216 which are created by dividing 3D image, and/or the computed slabs of 2D slices and/or 2D frames captured in real time, as described herein, may be stored in medical image repository 214, and/or in other locations such as memory 206 and/or data storage device 220 of computing device 204, on another server 218.

Computing device 204 may receive the 3D image and/or 2D frames, and/or sequence(s) of 2D anatomical image(s) via one or more imaging interfaces 226, for example, a wire connection (e.g., physical port), a wireless connection (e.g., antenna), a network interface card, other physical interface implementations, and/or virtual interfaces (e.g., software interface, application programming interface (API), software development kit (SDK), virtual network connection).

Memory 206 stores code instructions executable by hardware processor(s) 202. Exemplary memories 206 include a random access memory (RAM), read-only memory (ROM), a storage device, non-volatile memory, magnetic media, semiconductor memory devices, hard drive, removable storage, and optical media (e.g., DVD, CD-ROM). For example, memory 206 may code 206A that execute one or more acts of the method described with reference to FIGS. 1A and/or 1B.

Computing device 204 may include data storage device 220 for storing data, for example, GUI code 220A (which may present the summary images) and/or a neural network and/or encoder 220B from which encodings are extracted for determining the slabs, and/or one or more trained summary image machine learning models 220C which receive the summary image as input, and/or one or more trained 2D machine learning models 220D which receive a 2D image(s) selected from the slab as input as described herein. Data storage device 220 may be implemented as, for example, a memory, a local hard-drive, a removable storage unit, an optical disk, a storage device, a virtual memory and/or as a remote server 218 and/or computing cloud (e.g., accessed over network 210). It is noted that GUI 220A and/or neural network and/or autoencoder 220B and/or machine learning model(s) 220C may be stored in data storage device 220, for example, with executing portions loaded into memory 206 for execution by processor(s) 202.

Computing device 204 may include data interface 222, optionally a network interface, for connecting to network 210, for example, one or more of, a network interface card, a wireless interface to connect to a wireless network, a physical interface for connecting to a cable for network connectivity, a virtual interface implemented in software, network communication software providing higher layers of network connectivity, and/or other implementations.

Computing device 204 may connect using network 210 (or another communication channel, such as through a direct link (e.g., cable, wireless) and/or indirect link (e.g., via an intermediary computing unit such as a server, and/or via a storage device) with one or more of:

Client terminal(s) 208, for example, users using client terminals 208 to access computing device 204 for viewing summary images stored on the server (e.g., computing device 204 acts as the PACS server).

Server 218, for example, when server 218 is implemented as the PACS server, where users use client terminals 208 to access the PACS server. Computing device 204 provides enhanced features to the PACS server, receiving the 3D image and/or 2D real time frames from the PACS server, and providing the summary image(s) to the PACS server, where client terminals access the summary image(s) from the PACS server.

Medical image repository 214 that stores captured 3D images and/or 2D real time frames and/or the summary image(s).

Computing device 204 and/or client terminal(s) 208 and/or server(s) 218 include and/or are in communication with one or more physical user interfaces 224 that include a display for presenting the summary image(s) and/or 3D image and/or real time frames, and/or a mechanism for interacting with the summary image(s), such as zooming the summary image and/or marking finding on the summary image. Exemplary user interfaces 208 include, for example, one or more of, a touchscreen, a display, a keyboard, a mouse, and voice activated software using speakers and microphone.

Referring now back to FIG. 1A, at 102, a 3D medical image is received, for example, from the imaging device, from a PACS server, and/or from a data storage device.

The 3D medical image may depict one or more regions of the body, for example, full body scan, chest, abdomen, chest plus abdomen, head, and limbs.

The 3D medical image may be an anatomical image depicting anatomical structures within the body (e.g., organs), and/or a functional image depicting functional features within the body (e.g., nuclear scan, functional MRI).

Exemplary imaging modalities that generated 3D medical images include: CT, MRI, fMRI, breast tomography, 3D ultrasound, 3D nuclear imaging, and PET.

At 104, the 3D medical image is divided into a sequence of 2D images (sometimes referred to herein as slices). For example, a 3D CT image is divided into axial slices. Other slice angles may be used, for example, coronal slices, sagittal slices, and/or other angles.

Optionally, the 3D medical images are divided into the sequence of 2D images according to a slice orientation and/or a slice thickness and/or overlap of slices. The slice orientation and/or slice thickness may set according to the user and/or other users and/or standard radiology practice, for example, a history of the slice orientation and/or slice thickness that the user and/or other users previously selected for a similar 3D image (e.g., similar imaging modality and/or similar body part) and/or standard radiology practice for setting the slice orientation and/or slice thickness (e.g., according to imaging modality and/or body part). In other examples, the slice orientation and/or slice thickness may be set based on one or more of: system default value, manual selection by the user, based on the input into the neural network and/or encoder described herein, and/or automatic selection by code (e.g., to optimize the process described herein).

Optionally, the 3D medical image is pre-divided into the sequence of 2D images. For example, CT scans may already be stored and/or defined (e.g., by metadata) in terms of slice. The defined slices may be used.

At 106, a similarity dataset indicative of an amount of similarity between each pair of the 2D images is computed.

The pair of 2D images are neighboring sequential images. For example, for sequential images S1, S2, S3, S4, S5, S6 the pairs are S1-S2, S2-S3, S3-S4, S4-S5, and S5-S5, or in another example, the pairs are S1-S2, S3-S4, and S5-S6. Optionally, the similarity dataset is implemented as a matrix of size N×N where N denotes a number of the 2D images.

The amount of similarity of the similarity dataset may be computed by the following exemplary process. each 2D image is inputted into a neural network. The neural network may be trained to analyze a target 2D image and generate an outcome (i.e., output) of an indication of a target visual feature being depicted within the target 2D image. For example, the neural network may be trained to perform the same function the radiologist is performing, for example, to find nodules in lungs, and/or metastatic cancer in the body, and/or visual features indicative of appendicitis, and/or diverticulitis and/or kidney cancer and/or calcification in arteries. Alternatively, the neural network is trained to perform other functions, that the radiologist is not necessarily performing, for example, segmentation of the liver. The neural network may be selected from multiple neural networks each trained to output an indication of different respective visual features, which may be in different parts of the body. Alternatively, a single neural network is trained to output the multiple different respective features. The neural network may be selected manually and/or automatically, for example, according to the visual feature of the neural network (e.g., the user is viewing the 3D medical image to search for the visual feature), according to the images that the neural network is trained to process (e.g., CT scan, MRI, 3D US) that correspond to the input 2D images, and according to the body region that the neural network is trained to process (e.g., head, chest) that corresponds to the body region depicted in the input 2D images. The neural network may be the same neural network used by a radiologist support system that executes automated machine learning tools on the images to help the radiologist identify clinically significant visual findings.

For each 2D image inputted into the neural network, a feature vector is extracted from the neural network. The feature vector may be obtained from embeddings (e.g. values of weights of neurons) obtained from hidden layers of the neural network, and/or an output of an autoencoder implementation of the neural network where the feature vector is an output of the neural network. The autoencoder may be created from the neural network by removing certain layers of the neural network. The amount of similarity is computed for the feature vectors of each pair of 2D images, for example, using a cosine similarity computed for each pair, or other correlation functions that compute a value indicative of correlation between datasets.

In another exemplary approach, the plurality slabs are computed by inputting the sequential 2D images into a video scene analysis process. Each 2D image represents a frame in the video. The video scene analysis process may be a standard video scene analysis program that divides a video into scenes of frames. The scenes computed by the video scene analysis code correspond to the slabs described herein.

At 108, the similarity dataset is segmented into slabs by minimizing the amount of similarity between consecutive slabs and maximizing the amount of similarity within each slab. The 2D images included within each slab are more similar to one another than to other 2D images of other slabs. Segmentation may be performed, for example, using dynamic programming approaches. Segmentation may be performed, for example, using dynamic programming approaches, iterative trial and error (e.g., iteratively moving 2D images on the boundary between one group and the adjacent group), and/or clustering approaches, where each cluster represents a respective group with the added requirement that the images remain sequential.

At 110, for each respective slab, 2D images within the respective slab are aggregated into a respective summary image. In some embodiments, each respective summary image is a sequence of 2D images that summarizes a respective portion of the 2D image. In some embodiments, each respective summary image may be a 2D image that simulates an appearance of being a 3D image.

The summary image is computed using the 2D images of the respective slab. Alternatively or additionally, the summary image is computed from the 3D dataset portion of the 3D image that corresponds to the 2D images of the respective slab, for example, for a CT image with 1-500 slices, where the current slab is of slices 45-62, the summary image is computed using slices 45-62, and/or using the 3D dataset of the CT image (e.g., voxels, other data representation) that corresponds to slices 45-62.

The summary image may be computed, i.e., aggregated, by processes that compute summary images from the sequence of 2D images and/or from the 3D dataset of the 3D image corresponding to the 2D images, for example, for each respective slab, a maximum intensity projection (MIP) of the 2D images of the slab and/or the 3D portion of the 3D image corresponding to the slab. The summary image is the computed MIP. The MIP projects in the visualization plane the voxels with maximum intensity that fall in the way of parallel rays traced from the viewpoint to the plane of projection.

Other exemplary approaches for computing summary images from the sequence of 2D images and/or from the 3D dataset of the 3D image corresponding to the 2D images include, for example, local maximum intensity projection, average intensity projection, and volume rendering with high and/or low threshold.

Feature sets 112, 114-116, and 118-122, represent three exemplary uses of the computed summary image and/or computed slabs. One, two, or all three of the exemplary uses may be implemented. The exemplary uses may be performed, for example, in parallel, in sequence, and/or in any other order.

At 112, one or more of the summary images are provided. The summary images may be presented on a display, stored in a data storage device (e.g., by the PACS server, on a hard drive, on an external memory card, on a remote server), forwarded to another device (e.g., to a server, remote storage facility), and/or provided to another process (e.g., application) as input for further processing.

Optionally, one or more (e.g., all) of the summary images are presented on the display).

At 114, one or more of the summary images are inputted into a summary image machine learning (ML) model trained on a training dataset of sample summary images and corresponding finding(s) depicted therein indicative of ground truth. An indication of findings depicted in the respective summary image is obtained as an outcome of the summary image ML model. There may be multiple summary image ML models, each trained for a different body region and/or to identify different findings. Each summary image may be fed into all summary image ML models, and/or into one or more ML models selected from the multiple available ML models, for example, based on the summary image ML model corresponding to the neural network and/or encoder used to compute the feature vectors used to create the slabs, based on body part depicted within the slabs, and the like.

Optionally, the summary ML model is implemented using a simple deep neural network (DNN) and/or other computationally efficient ML model that processes 2D images. The summary ML is computationally more efficient than a 3D ML model that analyzes an input of a 3D dataset, for example, using 3D convolutions. The summary model may exclude other more complex designs used for analyzing 3D images, for example, the summary ML model may exclude a feature pyramid that processes inputted 3D images in resolutions and with box shapes.

The summary ML model may be implemented, for example, as a statistical classifier, and/or a neural network (of various architectures).

At 116, a score indicative of the presence of one or more findings depicted in the summary image is obtained as an outcome of the summary ML model. For example, the summary ML model generates a score indicative of likelihood of a malignancy being depicted in the inputted summary image. For example, likelihood of a pulmonary nodule, arterial calcification, and metastatic tumor being depicted within the respective summary image.

At 118, following 108 using the computed slabs, a subsample set one or more 2D images is selected from each respective slab. The images of the sub-sample may represent a selected sample of the slab, where findings depicted within the slab are likely to be depicted within the sub-sample.

The sub-sample includes fewer 2D images than the respective slab, for example, a single image, 2 images, 3 images, 5 images, or greater. The number of 2D images selected from each slab may be set as a percentage of the slab, for example, 10% of the 2D images, in the slab, or 5%, or 20%, or other values.

The 2D images of the sub-sample selected from the slab may be in predefined regions of the slab, for example, including one or both boundary 2D images that are sequentially adjacent to another slab, and/or the middle 2D image of the slab. The 2D images of the sub-sample may be selected using a defined pattern within the slab, for example, evenly spaced apart. The 2D images of the sub-sample may be randomly selected from the 2D images of the slab.

At 120, each 2D image of each respective sub-sample set of each respective slab is inputted into a 2D ML model. The 2D ML model is trained on a training dataset of sample 2D images and corresponding visual feature(s) depicted in the corresponding image indicative of ground truth.

Rather than analyzing each one of the 2D images of the slab by inputting each 2D imaging into the 2D ML model, the sub-sample images are analyzed by being inputted into the 2D ML model, which provides an overall state of the slab while significantly reducing the amount of computational resources used to analyze the model.

Optionally, the 2D ML model is implemented using a simple deep neural network (DNN) and/or other computationally efficient ML model that processes 2D images. The 2D ML is computationally more efficient than a 3D ML model that analyzes an input of a 3D dataset, for example, using 3D convolutions. The 2D model may exclude other more complex designs used for analyzing 3D images, for example, the 2D ML model may exclude a feature pyramid that processes inputted 3D images in resolutions and with box shapes.

The 2D ML model may be implemented, for example, as a statistical classifier, and/or a neural network (of various architectures).

At 122, a score indicative of the presence of one or more findings depicted in each respective 2D image is obtained as an outcome of the 2D ML model. For example, the 2D ML model generates a score indicative of likelihood of a malignancy being depicted in the inputted 2D image. For example, likelihood of a pulmonary nodule, arterial calcification, and metastatic tumor being depicted within the respective 2D image.

Referring now back to FIG. 1B, at 150, a 2D medical image captured in real time is received. The 2D image is part of a sequence of 2D images are captured by an imaging device during a real time imaging procedure. The imaging device may be, for example, a colonoscope, an endoscope, a bronchoscope, and a 2D ultrasound device.

The 2D image may be a captured still image, and/or as part of a stream of frames of a video. The captured 2D image of the video may be referred to herein as a frame.

The current 2D image may be part of an existing slab, which includes previously viewed 2D images. Alternatively, the current 2D image is part of a new slab that is different than the previously viewed slab.

Each slab of 2D images may correspond to a different anatomical location within the body of the subject being imaged.

It is noted that the process described with reference to FIG. 1B may be implemented offline, using previously acquired 2D images (i.e., not real time images). In such implementation, the 2D image is not a real time image, but a stored image captured during an imaging session, which is being viewed offline, for example, the user is viewing 2D images recorded during a colonoscopy session.

At 152, an amount of similarity between the current 2D medical image and one or more previously obtained sequence of 2D medical images, optionally the 2D medical image received prior to the current 2D medical image, is computed.

The amount of similarity be computed using the following exemplary process: the 2D image is inputted into a neural network trained to analyze a target 2D image and output an indication of a target visual feature being depicted within the target 2D image. A feature vector for the 2D image is extracted from the neural network. An amount of similarity between the feature vector of the current 2D image and feature vectors of the previously obtained sequence of 2D images (optionally the 2D image just prior to the current 2D image) is computed.

Additional exemplary details of computing the amount of similarity are described, for example, with reference to 106 of FIG. 1A.

At 154, the current (e.g., currently presented on a display) 2D medical image is analyzed to determine whether the current 2D medical image represents a last image (e.g., end), and/or is an intermediate part of an existing slab including one or more previously obtained sequence of 2D images, or whether the current 2D medical image is a first image of a new slab. It is noted that the current 2D medical image may be determined as representing the last image of an existing slab after one or multiple frames of a new slab have been received and have been determined to represent the new slab. Once a few (e.g., 1-5, or 2-10, or 2-5, or other ranges) of images are determined to belong to a new slab, the current 2D medical image (which is a previously obtained 2D medical image after the multiple new images of the new slab have been received) may be identified as the last image of the slab.

In the case of a captured video, where different slabs may correspond to different anatomical regions, multiple frames captured of the same anatomical region (e.g., the scope is held in the same location) may be part of the same slab. A new slab may be identified for images captured of another anatomical region (e.g., the scope is moved to the new anatomical location).

When the amount of similarity is above a threshold, indicating that the current 2D image is similar to the other previous images, the 2D medical image is part of the current slab, and feature 156 is implemented. Alternatively, when the amount of similarity is below the threshold, indicating that the current 2D image is not similar to the other previous images, the 2D medical image represents the end of the slab, and feature 158 is implemented.

At 156, in response to the 2D medical image not representing end of the slab, the current 2D medical image is defined as part of the current slab. Another performing iteration is performed, by iterating features 150-154 for another 2D medical image.

At 158 in response to the 2D medical image representing the end of the current slab and/or start of a new slab, one or more exemplary implementations representing exemplary uses of the computed slab are implemented. The three exemplary implementations are represented by feature sets 158-160, 158 and 162-164, and 166-170 (following 154 without necessarily implementing 158). One, two, or all three of the exemplary uses may be implemented. The exemplary uses may be performed, for example, in parallel, in sequence, and/or in any other order.

The sequentially obtained 2D images of the current slab are aggregated into a summary image. The summary image may be computed from the 2D images of the current slab, for example, using a MIP of the 2D images of the slab, where the summary image is the computed MIP. Additional exemplary details for computing the summary image found, for example, with reference to 110 of FIG. 1A.

At 160, the summary image is provided, optionally presented on a display. Additional exemplary details for providing the summary image, is found, for example, with reference to 112 of FIG. 1A.

At 162, the computed summary image is inputted into a summary image ML model trained on a training dataset of sample summary images and corresponding visual feature(s) depicted therein indicative of ground truth. Additional exemplary details for inputting the summary image into the summary image ML model found, for example, with reference to 114 of FIG. 1A.

At 164, a score of one or more visual findings depicted in the summary image is obtained as an outcome of the summary image ML model. Additional exemplary details for obtaining the score, is found, for example, with reference to 116 of FIG. 1A.

At 166, a sub-sample set of one or more 2D images is selected from the current slab. The sub-sample includes fewer 2D images than the respective slab. Additional exemplary details for selecting the 2D images from the slab, is found, for example, with reference to 118 of FIG. 1A.

At 168, the 2D image(s) of the sub-sample selected from the current respective slab is inputted into a 2D ML model trained on a training dataset of sample 2D images and corresponding visual feature(s) depicted therein indicative of ground truth.

Additional exemplary details for inputting the 2D images into the 2D ML model, is found, for example, with reference to 120 of FIG. 1A.

At 170, a score of one or more visual findings depicted in the 2D image is obtained as an outcome of the 2D ML model. Additional exemplary details for obtaining the score, is found, for example, with reference to 122 of FIG. 1A.

At 172, one or more features described with reference to 150-170 are iterated, for example, for each 2D real time image obtained throughout the imaging session and/or imaging procedure.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant 3D images and ML models will be developed and the scope of the terms 3D image and ML model are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computer implemented method for generating summary images from 3D medical images, comprising:
   receiving a 3D medical image;
   dividing the 3D medical images into a sequence of a plurality 2D images;
   computing a similarity dataset indicative of an amount of similarity between each pair of the plurality of 2D images;
   segmenting the similarity dataset into a plurality of slabs by minimizing the amount of similarity between consecutive slabs and maximizing the amount of similarity within each slab;
   aggregating, for each respective slab, the plurality of 2D images into a respective summary image; and
   presenting on a display, the respective summary image.

2. The method of claim 1, wherein aggregating comprises computing, for each respective slab, a maximum intensity projection (MIP) from the plurality of 2D images, wherein the summary image comprises the MIP.

3. The method of claim 1, further comprising:
   selecting a sub-sample set of at least one 2D image from each respective slab, wherein the sub-sample includes fewer 2D images than the respective slab;
   inputting each 2D image of each respective sub-sample set of each respective slab into a 2D machine learning model trained on a training dataset of a plurality of sample 2D images and corresponding at least one visual feature depicted therein indicative of ground truth; and
   obtaining a score indicative of the presence of at least one finding depicted in each 2D image as an outcome of the 2D machine learning model.

4. The method of claim 3, wherein the sub-sample set includes at least one boundary 2D image that is sequentially adjacent to another slab.

5. The method of claim 3, wherein the 2D machine learning model includes a simple deep neural network (DNN) and excludes a feature pyramid that processes inputted 3D images in a plurality of resolutions and with a plurality of box shapes.

6. The method of claim 1, wherein the similarity dataset is a matrix of size N×N wherein N denotes a number of the plurality of 2D images.

7. The method of claim 1, further comprising:
   inputting each 2D image into a neural network trained to analyze a target 2D image and output an indication of a target visual feature being depicted within the target 2D image;
   extracting, for each 2D image, a feature vector from the neural network;
   wherein the amount of similarity is computed for the feature vectors of each pair.

8. The method of claim 7, wherein the amount of similarity is computed for the feature vectors of each pair using a cosine similarity.

9. The method of claim 7, wherein the feature vector is selected from the group consisting of: embeddings obtained from hidden layers of the neural network, an output of an autoencoder implementation of the neural network, and the feature vector is an output of the neural network.

10. The method of claim 9, further comprising selecting the neural network from a plurality of neural networks each trained to output an indication of a different visual feature, according to the visual feature, wherein the user is viewing the 3D medical image to search for the visual feature.

11. The method of claim 1, wherein the plurality of slabs are computed by inputting the sequential 2D images into a video scene analysis process that divides a video into scenes of frames, the 2D images corresponding to frames of the video and the scenes corresponding to slabs.

12. The method of claim 1, wherein the 3D medical image is selected from the group consisting of: CT, MRI, breast tomography, 3D ultrasound, 3D nuclear imaging, and PET.

13. The method of claim 1, wherein the 3D medical images are divided into a sequence of a plurality 2D images according to a slice orientation and/or a slice thickness defined by the user viewing the plurality of 2D images and corresponds to the slice orientation and/or slice thickness when the user views the plurality of 2D images.

* * * * *